United States Patent
Rausch et al.

(10) Patent No.: US 10,973,417 B2
(45) Date of Patent: Apr. 13, 2021

(54) NONINVASIVE PRESSURE MONITORING

(71) Applicant: Nonin Medical, Inc., Plymouth, MN (US)

(72) Inventors: Gregory J. Rausch, Minnetonka, MN (US); Timothy L. Johnson, Plymouth, MN (US); Matthew Prior, Plymouth, MN (US)

(73) Assignee: Nonin Medical, Inc., Plymouth, MN (US)

( * ) Notice: Subject to any disclaimer, the term of this patent is extended or adjusted under 35 U.S.C. 154(b) by 400 days.

(21) Appl. No.: 15/316,784

(22) PCT Filed: Jun. 5, 2015

(86) PCT No.: PCT/US2015/034498
§ 371 (c)(1),
(2) Date: Dec. 6, 2016

(87) PCT Pub. No.: WO2015/188108
PCT Pub. Date: Dec. 10, 2015

(65) Prior Publication Data
US 2017/0188855 A1 Jul. 6, 2017

Related U.S. Application Data

(60) Provisional application No. 62/082,715, filed on Nov. 21, 2014, provisional application No. 62/008,938, filed on Jun. 6, 2014.

(51) Int. Cl.
*A61B 5/03* (2006.01)
*A61B 5/022* (2006.01)
(Continued)

(52) U.S. Cl.
CPC .......... *A61B 5/02116* (2013.01); *A61B 5/022* (2013.01); *A61B 5/0205* (2013.01);
(Continued)

(58) Field of Classification Search
None
See application file for complete search history.

(56) References Cited

U.S. PATENT DOCUMENTS

| 5,564,435 A | 10/1996 | Steinberg |
| 5,715,828 A | 2/1998 | Raines et al. |

(Continued)

FOREIGN PATENT DOCUMENTS

| EP | 1374761 A2 | 1/2004 |
| JP | 06070702 | 4/1994 |

(Continued)

OTHER PUBLICATIONS

Smyth et al. (The Guard-Ring Tocodynamometer Absolute Measurement of Intra-Amniotic Pressure by a New Instrument) Journal of Obstetrics and Gwaecology; 1957 (Year: 1957).*

(Continued)

*Primary Examiner* — Kaylee R Wilson
*Assistant Examiner* — Jay B Shah
(74) *Attorney, Agent, or Firm* — Schwegman Lundberg & Woessner, P.A.

(57) ABSTRACT

A method includes affixing a co-planar sensor on a surface, using a processor, and providing an output. The method includes affixing a co-planar sensor on a surface at a first tissue site. The sensor has a force transducer disposed at an aperture of a rigid guard member. The guard member and the transducer are in co-planar alignment. The transducer is configured to provide an electrical signal corresponding to an internal pressure at the first tissue site. The method includes using the processor to compare the internal pressure with a reference value. Based on the comparison, the method includes providing an output corresponding to compartment syndrome at the first tissue site.

16 Claims, 5 Drawing Sheets

(51) Int. Cl.
  *A61B 5/1455* (2006.01)
  *A61B 5/021* (2006.01)
  *A61B 5/00* (2006.01)
  *A61B 5/0205* (2006.01)
  *A61B 5/024* (2006.01)

(52) U.S. Cl.
  CPC ...... *A61B 5/02108* (2013.01); *A61B 5/02125* (2013.01); *A61B 5/02233* (2013.01); *A61B 5/031* (2013.01); *A61B 5/14552* (2013.01); *A61B 5/7242* (2013.01); *A61B 5/02427* (2013.01); *A61B 2562/0247* (2013.01)

(56) References Cited

U.S. PATENT DOCUMENTS

| | | | |
|---|---|---|---|
| 2001/0020133 A1* | 9/2001 | Ito | A61B 5/02125 600/483 |
| 2006/0009700 A1* | 1/2006 | Brumfield | A61B 5/0261 600/504 |
| 2006/0200015 A1 | 9/2006 | Baker | |
| 2010/0081941 A1 | 4/2010 | Naghavi et al. | |
| 2010/0094140 A1 | 4/2010 | Pranevicius et al. | |
| 2010/0168596 A1* | 7/2010 | Jaeschke | A61B 5/02411 600/511 |
| 2013/0006121 A1 | 1/2013 | Myers | |

FOREIGN PATENT DOCUMENTS

| | | |
|---|---|---|
| JP | 2002010986 A | 1/2002 |
| JP | 6319712 | 5/2018 |
| JP | 6612335 | 11/2019 |
| WO | WO-2012140510 A2 | 10/2012 |
| WO | WO-2013/001265 A2 | 1/2013 |
| WO | WO-2015188108 A1 | 12/2015 |

OTHER PUBLICATIONS

Elgendi, On the Analysis of Fingertip Photoplethysmogram Signals; Current Cardiology Reviews, 2012, 8, 14-25 (Year: 2012).*

International Application Serial No. PCT/US2015/034498, Invitation to Pay Additional Fees and Partial Search Report dated Aug. 21, 2015, 2 pgs.

International Application Serial No. PCT/US2015/034498, International Search Report dated Nov. 3, 2015, 4 pgs.

International Application Serial No. PCT/US2015/034498, Written Opinion dated Nov. 3, 2015, 5 pgs.

Gallagher, Dympna, et al., "Quantitative Magnetic Resonance Fat Measurements in Humans Correlate With Established Methods but are Biased", Obesity, (2010), 2047-2054.

Hollinger, Avrum, et al., "Evaluation of Commercial Force-Sensing Resistors", NIME06, (2006).

"European Application Serial No. 15802767.2, Response filed Nov. 19, 2018 to Extended European Search Report dated Apr. 16, 2018", 8 pgs.

"European Application Serial No. 15802767.2, Extended European Search Report dated Apr. 16, 2018", 12 pgs.

"Japanese Application Serial No. 2017-516641, Response filed Mar. 15, 2019 to Notification of Reasons for Rejection dated Dec. 18, 2018", with English Claims, 11 pgs.

"Japanese Application Serial No. 2017-516641, Notification of Reasons for Rejection dated Apr. 2, 2019", with English Translation, 6 pgs.

Japanese Application Serial No. 2017-516641, Notification of Reasons for Rejection dated Dec. 18, 2018, W/ English Translation, 8 pgs.

"European Application Serial No. 15802767.2, Communication pursuant to Rule 164(1) EPC dated Jan. 3, 2018", 14 pgs.

"Canadian Application Serial No. 2,951,375, Office Action dated Jun. 22, 2020", 6 pgs.

"Canadian Application Serial No. 2,951,375, Voluntary Amendmnet filed Jun. 5, 2020", 8 pgs.

* cited by examiner

NONINVASIVE PRESSURE MONITORING

CLAIM OF PRIORITY

This patent application is a U.S. National Stage Filing under 35 U.S.C. 371 from International Application No. PCT/US2015/034498, filed on Jun. 5, 2015, and published as WO 2015/188108 A1 on Dec. 10, 2015 which claims the benefit of priority of U.S. Provisional Patent Application Ser. No. 62/008,938, filed on Jun. 6, 2014, and claims the benefit of priority of U.S. Provisional Patent Application Ser. No. 62/082,715, filed on Nov. 21, 2014, each of which is hereby incorporated by reference herein in its entirety.

BACKGROUND

A healthy body will have normal internal pressures within various organs and regions of a body. As a result of a disorder, injury or medical condition, the pressure can become excessive. For example, compartment syndrome refers to a medical condition characterized by an abnormal increase in pressure within a limb and intracranial pressure (ICP) refers to excessive pressure in the cranium.

The pressure associated with compartment syndrome is the result of blood flowing into a region and impaired blood discharge leading to tissue swelling. Left unchecked, this condition can lead to tissue damage in mild cases and to amputation of a limb or death in more severe cases.

One common treatment for compartment syndrome includes a surgical procedure known as fasciotomy. Fasciotomy entails a series of incisions tailored to relieve pressure within a compartment. Fasciotomy, however, is not without complications, notably pain and risk of infection.

Overview

Diagnosis of internal pressure, such as compartment syndrome, is typically based on observed symptoms. The present inventors have recognized, among other things, that compartment syndrome and other pressure-related conditions can be detected and monitored using data from a non-invasive sensor.

According to one example, a device includes a plethysmograph and a processor. The plethysmograph is configured to provide a signal corresponding to a cyclic physiological parameter in a region of tissue. The processor is configured to execute instructions to implement an algorithm using the signal. The processor is configured to generate an output corresponding to pressure in the region.

A method includes affixing a co-planar sensor on a surface, using a processor, and providing an output. The method includes affixing a co-planar sensor on a surface at a first tissue site. The sensor has a force transducer disposed at an aperture of a rigid guard member. The guard member and the transducer are in co-planar alignment. The transducer is configured to provide an electrical signal corresponding to an internal pressure at the first tissue site. The method includes using the processor to compare the internal pressure with a reference value. Based on the comparison, the method includes providing an output corresponding to compartment syndrome at the first tissue site.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
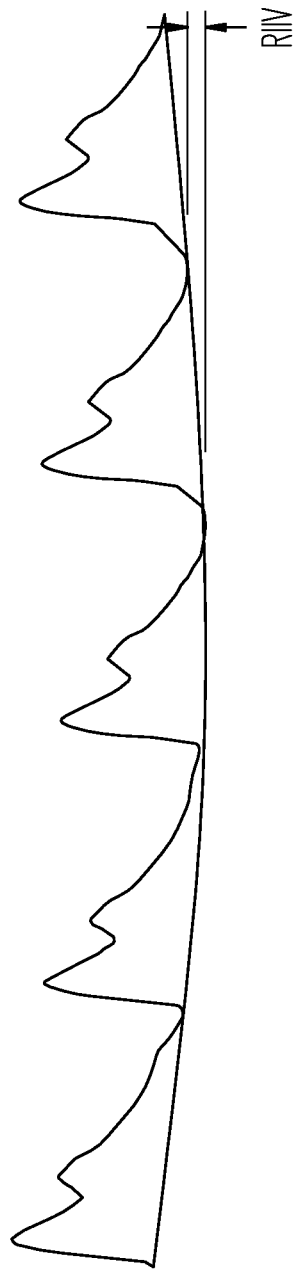
FIGS. 1A and 1B illustrate a photoplethysmograph.
Figure 1B:
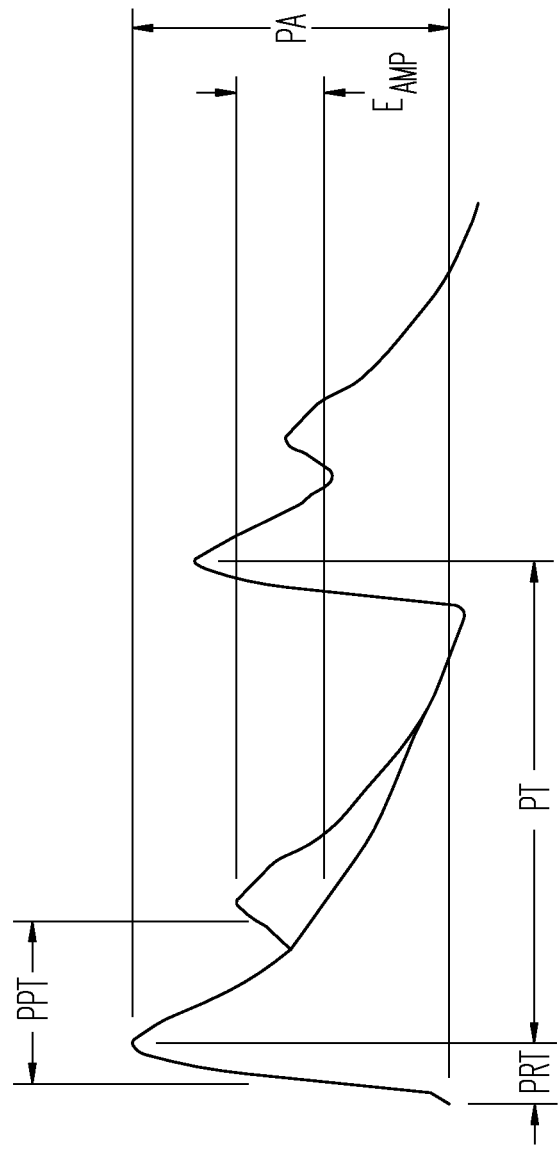

FIGS. 1A and 1B illustrate views of a photoplethysmograph. The plethysmograph indicates the time-varying volumetric change of an organ or tissue region resulting from pressure fluctuations caused by the cardiac cycle, the respiratory cycle, or both the cardiac and respiratory cycle. Various methods may be used to create the plethysmograph, including pneumatic devices such as an inflatable cuff and photometric devices such as a pulse oximeter. A photoplethysmograph (or PPG) refers to a photometrically-derived plethysmograph.

The volumetric change from pulsating blood in a tissue region is largely determined by the difference between the arterial pressure and the interstitial fluid pressure of the tissues surrounding the arterial-side blood vessels (arteries, arterioles, and capillaries). This pressure difference is commonly referred to as transmural pressure; the pressure across the wall of a blood vessel. Among other things, the magnitude of the plethysmographic signal is proportional to the transmural pressure. Variations in pressure, such as that noted in a plethysmographic signal, can indicate abnormal conditions such as compartment syndrome or increased intracranial pressure (conditions that can change the transmural pressure from normal levels). These variations can be sensed and calibrated to provide information regarding internal pressure. The information as to the internal pressure, either alone or in conjunction with regional oxygenation measurements (rSO2), can be used by a clinician in diagnosing the onset of localized ischemia. The shape of the PPG can vary significantly from subject to subject so the analyses of trends over time are of interest.

FIG. 1A illustrates a series of pulses that vary according to a respiration rate. In the figure, the respiratory-induced intensity variation is denoted as RIIV.

A variety of pulse features are shown in FIG. 1B. For example, the figure illustrates the pulse propagation time (PPT), the echo amplitude (Eamp), pulse amplitude (PA), pulse timing (PT), and pulse rise time (PRT).

The sensitivity to tissue pressure under the sensor can be improved by evaluating certain parameters (some examples include Eamp, PPT, or PRT) or measures of these parameters. For example, pressure can be correlated with a peak value, an average value, a measure of variation (such as standard deviation), or by evaluating an area under a curve (AUC) associated with one or more parameters. These features also correlate to diastolic and systolic blood pressures. These parameters can be used to monitor trends in blood pressure and site specific trends in interstitial pressure. These metrics, when combined, give the clinician indicators regarding the perfusion of the tissue in question.

Standard rSO$_2$ sensors include one or more sources of optical energy and one or more optical energy sensing elements. Various PPG parameters can be combined in many different fashions. The spacing of the different optical sensing elements can be referenced to each other to evaluate, for example, specific measureable trends. PPG parameters can also be referenced to control sensors on other locations of the body, again looking for trends.

Figure 2:
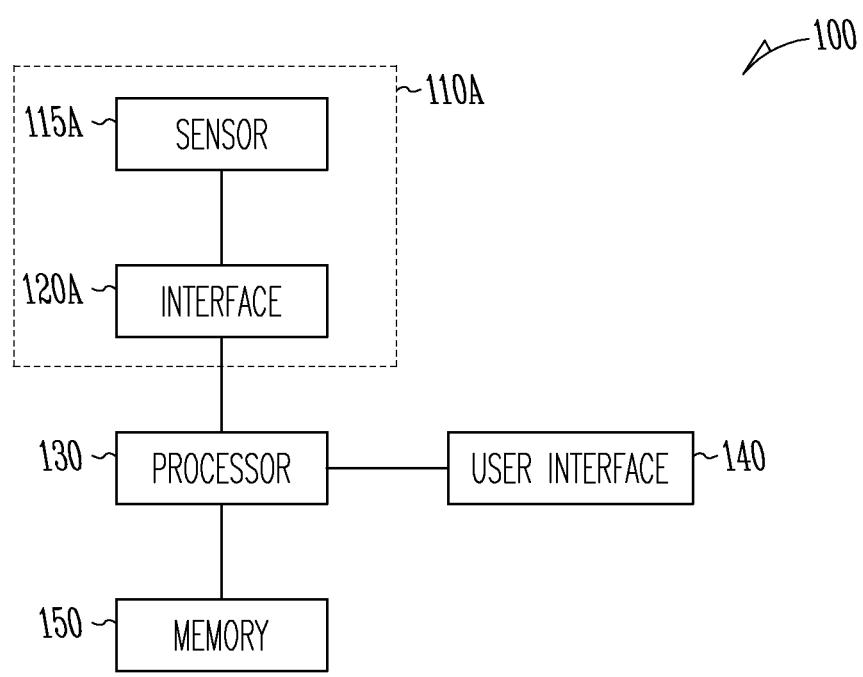
FIG. 2 includes a block diagram of a system, according to one example.

FIG. 2 includes a block diagram of system 100, according to one example. System 100 includes input module 110A coupled to processor 130. Processor 130 is also coupled to user interface 140 and memory 150.

Input module 110A, in the example shown, includes sensor 115A and interface 120A. In one example, sensor 115A can include an element configured to provide a signal corresponding to pressure within a tissue. Sensor 115A can include an optical emitter and an optical detector. Interface 120A can include an analog-to-digital converter (ADC), a digital-to-analog converter (DAC), an amplifier, a filter, or other circuitry tailored to condition the data (such as an electrical signal) provided to processor 130.

Processor 130 is configured to receive data from input module 110A. In one example processor 130 provides a signal to input module 110A to control operation of an element of input module 110A.

Memory 150 can provide storage for instructions for execution by processor 130. Memory 150 can provide storage for comparison (reference) data, trend data, calibration information, parameters, or results of processing.

User interface 140 can include a keyboard, a touch-sensitive screen, a mouse or cursor control, a printer, a display, a network interface, or other element configured to receive data from processor 130 or configured to provide data to processor 130.

Figure 3A:
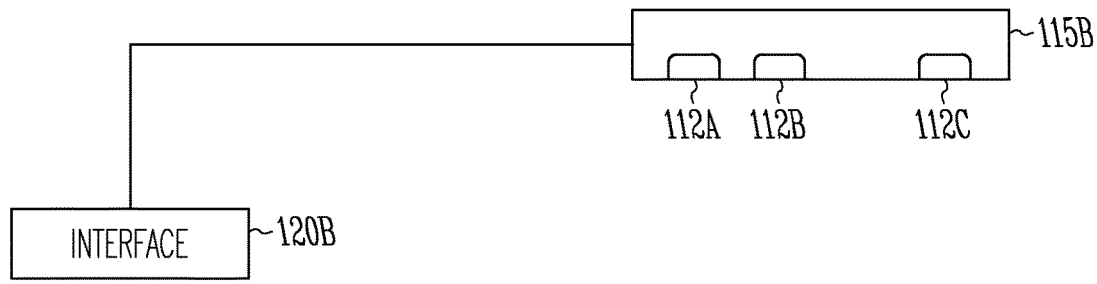
FIG. 3A includes a diagram of an input module, according to one example.

FIG. 3A includes a diagram of input module 110B. Input module 110B includes interface 120B coupled to sensor 115B. In the figure, sensor 115B includes three elements, here denoted as element 112A, element 112B, and element 112C, each of which are positioned on a surface of sensor 115B. Light emitted from an element is directed onto tissue positioned adjacent the surface (bottom) of sensor 115B.

Elements 112A, 112B, and 112C can include any combination of optical emitters and optical detectors. An optical emitter can include a light emitting diode (LED). An optical detector can include a photodetector. For example, element 112C can include an optical emitter and elements 112A and 112B can include optical detectors. The spacing of the elements on the surface of sensor 115B can be configured to correspond with a selected depth of penetration of light energy into a tissue. As shown, sensor 115B includes three elements, however, more than three or fewer than three can also be provided. In various examples, one or two optical emitters are provided on the surface of the sensor. In addition, an emitter can be configured to emit light at multiple different wavelengths.

Interface 120B is coupled to sensor 115B by a bidirectional link. Interface 120B is configured to exchange data or exchange signals with sensor 115B. In addition, interface 120B also is in communication with a processor, such as processor 130 (FIG. 2).

Figure 3B:
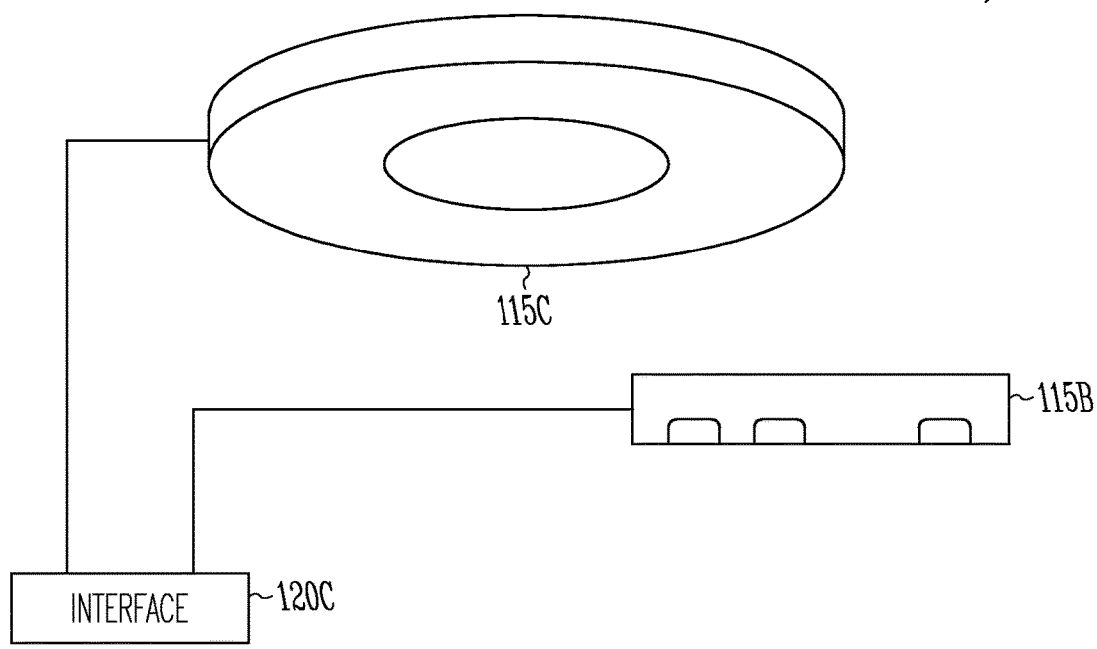
FIG. 3B includes a diagram of an input module, according to one example.

FIG. 3B includes a diagram of input module 110C, according to one example. Input module 110C includes interface 120C coupled to both sensor 115B and coupled to sensor 115C.

Sensor 115B is described elsewhere in this document, and in the example shown here, includes three optical elements disposed on a contact surface. Sensor 115C includes a pressure sensor having a planar surface and is sometimes referred to as a co-planar sensor ring or tocodynamometer. A co-planar sensor ring includes a guard ring and a centrally-located force sensor. The force sensor has a sense surface that is substantially co-planar with the guard ring. The guard ring, when urged against a tissue surface, will flatten the tissue in the manner of a diaphragm and the force sensor, held in contact with the diaphragm, provides a measure of a tissue pressure in the local region.

Interface 120C is coupled to both sensor 115B and sensor 115C by bidirectional links. Interface 120C is configured to exchange data or exchange signals with sensor 115B and with sensor 115C. In addition, interface 120C also is in communication with a processor, such as processor 130.

Figure 3C:
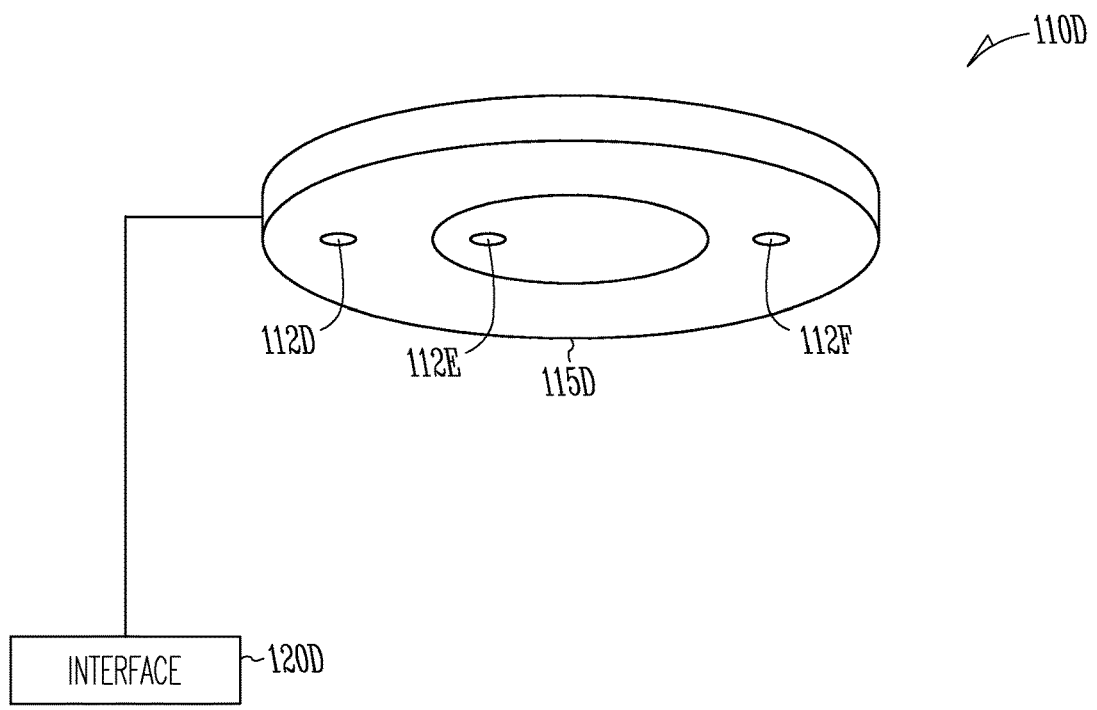
FIG. 3C includes a diagram of an input module, according to one example.

FIG. 3C includes a diagram of input module 110D, according to one example. Input module 110D includes interface 120D coupled to sensor 115D.

Sensor 115D includes three optical elements, here denoted as element 112D, 112E, and 112F, disposed on a contact surface configured as a guard ring of a tocodynamometer ring sensor.

Interface 120D is coupled to sensor 115D by bidirectional links. Interface 120D is configured to exchange data or exchange signals with sensor 115D. In addition, interface 120C also is in communication with a processor, such as processor 130.

In one example, interface 120D (in conjunction with processor 130) can independently control operation of the tocodynamometer ring sensor and the optical elements 112D, 112E, and 112F.

Figure 3D:
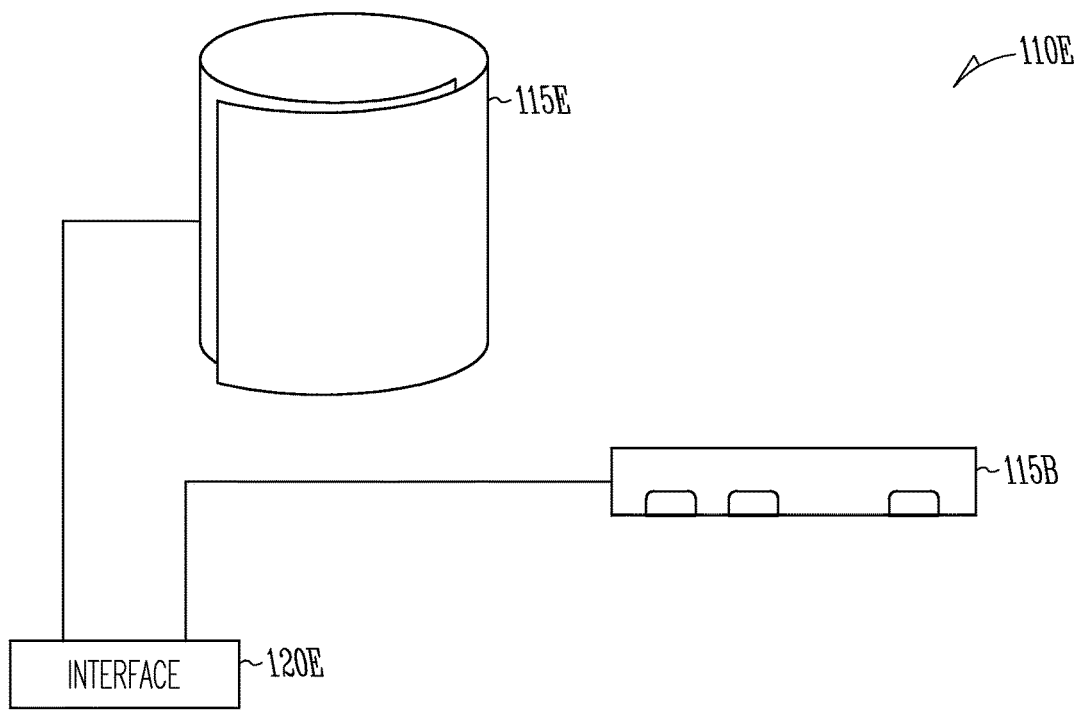
FIG. 3D includes a diagram of an input module, according to one example.

FIG. 3D includes a diagram of input module 110E, according to one example. Input module 110E includes interface 120E coupled to both sensor 115B and coupled to sensor 115E.

Sensor 115B is described elsewhere in this document, and in the example shown here, includes three optical elements disposed on a contact surface. Sensor 115E is illustrated here as a pressure cuff. The pressure cuff is configured to encircle a limb of patient and provide a measure of blood pressure. Pneumatic pressure within a chamber of the blood pressure cuff is modulated and a sensor element associated with the cuff provides an electrical signal (corresponding to blood pressure) to interface 120E.

Interface 120E is coupled to both sensor 115B and sensor 115E by bidirectional links. Interface 120E is configured to exchange data or exchange signals with sensor 115B and with sensor 115E. In addition, interface 120E also is in communication with a processor, such as processor 130.

Figure 4:
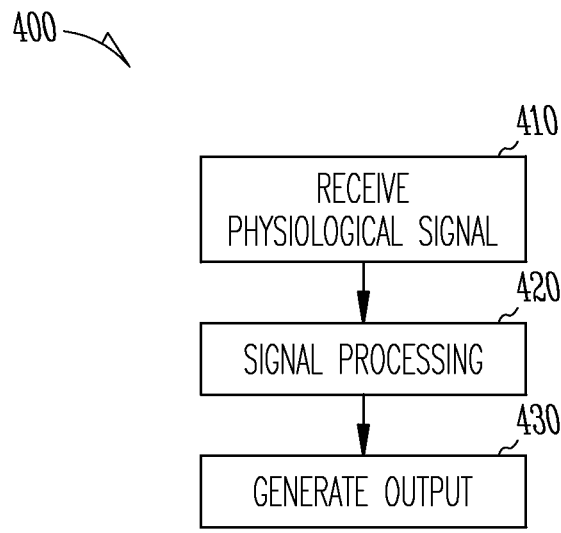
FIG. 4 includes a flow chart of a method, according to one example.

FIG. 4 includes a flow chart of method 400, according to one example. Method 400, at 410, includes receiving a physiological signal. The physiological signal can include receiving data corresponding to data derived from one or more optical elements. For example, the data can correspond to light attenuation based on scattered light, reflected light, attenuated light associated with a tissue site of a patient. In various examples, the physiological signal can include blood pressure data or tissue data (such as from a tocodynamometer ring sensor).

Method 400, at 420, can include signal processing. Signal processing can include filtering the data or amplifying the data. In addition, signal processing can include calculating a local maxima or minima, a peak value, an area under a curve, or a difference in amplitude or phase. In various examples, signal processing includes analysis of data in a time domain representation or in a frequency domain representation. Signal processing can also include comparing measure data with reference data stored, for example, in memory 150 (FIG. 2).

Method 400, at 430, can include generating an output. The output can be rendered on a visual display, on a touch sensitive screen, in the form of an audio signal (or alarm), or in other forms. In one example, the output is encoded and communicated using a network that spans a local area or a wide area. The network can include elements that communicate by a wired or wireless link.

Figure 5:
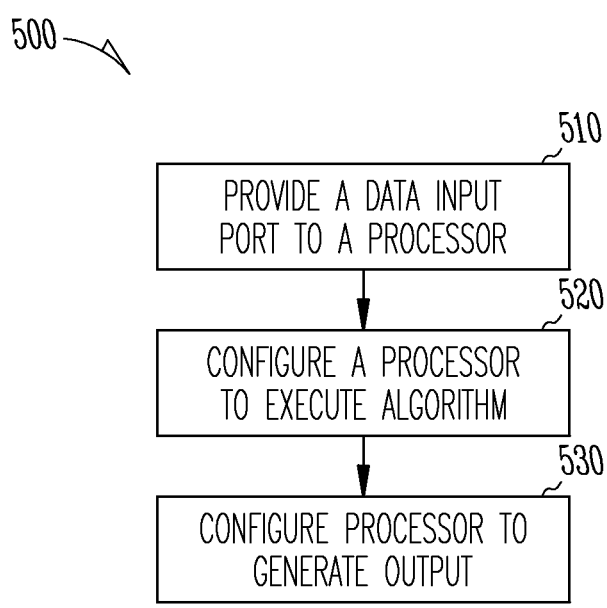
FIG. 5 includes a flow chart of a method, according to one example.

FIG. 5 includes a flow chart of method 500, according to one example. Method 500, at 510, includes providing a data input port to a processor. The data processor can be an analog or digital processor such as processor 130 shown in FIG. 2. The data input port can include a wired connector or can include a wireless telemetry module, one example of which includes a Bluetooth connection.

Method 500, at 520, includes configuring the processor to execute an algorithm. This can include providing circuitry to implement analog processing of data or providing executable instructions for execution by a digital processor. The instructions can be configured to control a sensor element in order to generate data indicative of pressure at a tissue site. For example, a measure of an area under a curve, in conjunction with optical data derived from a non-invasive sensor, can be processed using an algorithm.

Method 500, at 530, includes configuring the processor to generate an output. This can include coupling a processor to a visual display and programming the processor to render data depicting a measure of pressure at a tissue site.

VARIOUS NOTES & EXAMPLES

Example 1 can include or use subject matter (such as an apparatus, a method, a means for performing acts, or a device readable medium including instructions that, when performed by the device, can cause the device to perform acts), such as can include or use affixing a co-planar sensor on a surface at a first tissue site, the sensor having a force transducer disposed at an aperture of a rigid guard member, the guard member and the transducer in co-planar alignment and wherein the transducer is configured to provide an electrical signal corresponding to an internal pressure at the first tissue site; using a processor to compare the internal pressure with a reference value; and based on the comparison, providing an output corresponding to compartment syndrome at the first tissue site.

Example 2 can include, or can optionally be combined with the subject matter of Example 1, to optionally include wherein affixing the co-planar sensor includes applying a tensile force on a belt coupled to the sensor.

Example 3 can include, or can optionally be combined with the subject matter of one or any combination of Examples 1 or 2 to optionally include wherein affixing the co-planar sensor includes urging the sensor against the first tissue site.

Example 4 can include, or can optionally be combined with the subject matter of one or any combination of Examples 1 through 3 to optionally include wherein using the processor to compare the internal pressure with the reference value includes comparing the internal pressure with a measure of pressure at a second tissue site, the second tissue site different than the first tissue site.

Example 5 can include, or can optionally be combined with the subject matter of Example 4 to optionally include affixing a remote pressure sensor at the second tissue site, the remote pressure sensor having an electrical terminal and wherein comparing the internal pressure with the measure of pressure at the second tissue site includes comparing with a pressure signal on the electrical terminal.

Example 6 can include, or can optionally be combined with the subject matter of one or any combination of Examples 1 through 5 to optionally include wherein using the processor to compare the internal pressure with the reference value includes comparing the internal pressure with a stored value.

Example 7 can include, or can optionally be combined with the subject matter of one or any combination of Examples 1 through 6 to optionally include wherein providing the output corresponding to compartment syndrome includes providing a visible indication.

Example 8 can include, or can optionally be combined with the subject matter of one or any combination of Examples 1 through 7 to optionally include wherein providing the output corresponding to compartment syndrome includes wirelessly communicating the output.

Example 9 can include or use subject matter (such as an apparatus, a method, a means for performing acts, or a device readable medium including instructions that, when performed by the device, can cause the device to perform acts), such as can include or use a plethysmograph configured to provide a signal corresponding to a cyclic physiological parameter in a region of tissue; and a processor configured to execute instructions to implement an algorithm using the signal, the processor configured to generate an output corresponding to pressure in the region.

Example 10 can include, or can optionally be combined with the subject matter of Example 9, to optionally include wherein the plethysmograph includes an optical sensor.

Example 11 can include, or can optionally be combined with the subject matter of Example 10 to optionally include wherein the optical sensor includes a pulse oximeter sensor.

Example 12 can include, or can optionally be combined with the subject matter of one or any combination of Examples 10 or 11 to optionally include wherein the optical sensor includes a regional oximeter sensor.

Example 13 can include, or can optionally be combined with the subject matter of one or any combination of Examples 10 through 12 to optionally include wherein the optical sensor includes a first light emitter and a second light emitter.

Example 14 can include, or can optionally be combined with the subject matter of one or any combination of Examples 9 through 13 to optionally include wherein the plethysmograph includes a sensor and a pneumatic chamber.

Example 15 can include, or can optionally be combined with the subject matter of Example 14 to optionally include wherein the pneumatic chamber includes an inflatable cuff.

Example 16 can include, or can optionally be combined with the subject matter of one or any combination of Examples 9 through 15 to optionally include wherein the plethysmograph includes a force sensor and fixed support structure.

Example 17 can include, or can optionally be combined with the subject matter of one or any combination of Examples 9 through 16 to optionally include wherein the plethysmograph includes a includes a guard ring and a centrally-located force sensor.

Example 18 can include, or can optionally be combined with the subject matter of one or any combination of Examples 9 through 17 to optionally include wherein the processor is configured to calculate an echo amplitude corresponding to the signal.

Example 19 can include, or can optionally be combined with the subject matter of one or any combination of Examples 9 through 18 to optionally include wherein the processor is configured to calculate an area under a curve, wherein the curve is determined by a time domain representation of the signal.

Example 20 can include, or can optionally be combined with the subject matter of one or any combination of Examples 9 through 19 to optionally include wherein the processor is configured to calculate a pulse propagation time for the signal.

Example 21 can include, or can optionally be combined with the subject matter of one or any combination of Examples 9 through 20 to optionally include wherein the processor is configured to calculate a pulse rise time for the signal.

Example 22 can include, or can optionally be combined with the subject matter of one or any combination of Examples 9 through 21 to optionally include wherein the processor is configured to generate the output based on a trend.

Example 23 can include or use subject matter (such as an apparatus, a method, a means for performing acts, or a device readable medium including instructions that, when performed by the device, can cause the device to perform acts), such as can include or use configuring a processor to receive a plethysmograph signal, the plethysmograph signal corresponding to a cyclic physiological parameter corresponding to a region of tissue; and programming the processor to implement an algorithm using the signal, the processor configured to generate an output corresponding to pressure in the region.

Example 24 can include, or can optionally be combined with the subject matter of Example 23, to optionally include wherein configuring the processor to receive the plethysmograph signal includes configuring the processor to receive the signal from an optical sensor.

Example 25 can include, or can optionally be combined with the subject matter of one or any combination of Examples 23 or 24 to optionally include wherein configuring the processor to receive the plethysmograph signal includes configuring the processor to control an optical emitter.

Example 26 can include, or can optionally be combined with the subject matter of one or any combination of Examples 23 through 25 to optionally include wherein configuring the processor to receive the plethysmograph signal includes configuring the processor to control a pressure in a pneumatic chamber.

Example 27 can include, or can optionally be combined with the subject matter of one or any combination of Examples 23 through 26 to optionally include wherein programming the processor to implement the algorithm includes programming to calculate an echo amplitude corresponding to the signal.

Example 28 can include, or can optionally be combined with the subject matter of one or any combination of Examples 23 through 27 to optionally include wherein programming the processor to implement the algorithm includes programming to calculate an area under a curve, wherein the curve is determined by a time domain representation of the signal.

Example 29 can include, or can optionally be combined with the subject matter of one or any combination of Examples 23 through 28 to optionally include wherein programming the processor to implement the algorithm includes programming to calculate a pulse propagation time for the signal.

Example 30 can include, or can optionally be combined with the subject matter of one or any combination of Examples 23 through 29 to optionally include wherein programming the processor to implement the algorithm includes programming to calculate a pulse rise time for the signal.

Example 31 can include, or can optionally be combined with the subject matter of one or any combination of Examples 23 through 30 to optionally include wherein programming the processor to implement the algorithm includes programming to identify a trend.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device comprising:
   a photoplethysmograph that includes, a first sensor and a regional oximeter sensor configured to be disposed at a surface of a region of tissue, wherein the first sensor has a combination of one or more optical emitters and one or more optical detectors, wherein a spacing of the one or more optical emitters and one or more optical detectors on a surface of the first sensor that interfaces with the surface of the region of tissue is configured to correspond with a selected depth of penetration of light energy into the region of tissue, wherein the first sensor is configured to provide a first electrical signal corresponding to a pressure at the surface of the region of tissue and the regional oximeter sensor is configured to provide a second electrical signal corresponding to an oxygenation at the surface of the region of tissue; and
   a processor configured to execute instructions to implement an algorithm using the first electrical signal and the second electrical signal as inputs to generate an output corresponding to an internal pressure in the region, wherein the processor implements the algorithm to determine a transmural pressure of the region of tissue from a magnitude of the first electrical signal and wherein the processor implements the algorithm to monitor trends over a period of time in the first electrical signal that comprise at least one of an echo amplitude comprising a diastolic peak of the first signal, a pulse propagation time of the first signal, and a pulse rise time of the first signal that correspond to trends in pressure and trends in interstitial pressure in the region of tissue.

2. The device of claim 1 further comprising a pneumatic chamber.

3. The device of claim 2 wherein the pneumatic chamber includes an inflatable cuff.

4. The device of claim 1 further comprising a rigid guard member configured to be disposed at the surface of the region of tissue, wherein the rigid guard member includes a force transducer at an aperture of the guard member, and wherein force transducer is centrally located in the guard member.

5. The device of claim 1 wherein the processor implements the algorithm to calculate an area under a curve, wherein the curve is determined by a time domain representation of the first signal.

6. The device of claim 1 wherein the spacing of the one or more optical emitters and one or more optical detectors on the surface of the first sensor is referenced by the processor that implements the algorithm to evaluate the trends over the period of time in the first electrical signal.

7. The device of claim 1 wherein the first signal is referenced to a third signal from a control sensor coupled to another region of tissue by the processor that implements the algorithm to evaluate the trends over the period of time in the first electrical signal.

8. The device of claim 1 wherein the pressure is correlated with one or more of a peak value, an average value, a measure of variation, or an area under a curve associated with the first electrical signal that comprise at least one of the echo amplitude of the first signal, the pulse propagation time, and the pulse rise time.

9. A method comprising:
   providing a photoplethysmograph that includes a first sensor and a regional oximeter sensor configured to be disposed at a surface of a region of tissue, wherein the first sensor has a combination of one or more optical emitters and one or more optical detectors, wherein a spacing of the one or more optical emitters and one or more optical detectors on a surface of the first sensor that interfaces with the surface of the region of tissue is configured to correspond with a selected depth of penetration of light energy into the region of tissue, wherein the first sensor is configured to provide a first electrical signal corresponding to a pressure at the surface of the region of tissue and the regional oximeter sensor is configured to provide a second electrical signal corresponding to an oxygenation at the surface of the region of tissue;
   configuring a processor to receive a first electrical signal corresponding to a pressure at the surface of the region of tissue and a second signal from the regional oximeter sensor corresponding to an oxygenation at the surface of the region of tissue; and
   programming the processor to implement an algorithm using the first signal and the second signal as inputs to generate an output corresponding to an internal pressure in the region, wherein the processor implements the algorithm to determine a transmural pressure of the region of tissue from a magnitude of the first electrical signal and wherein the processor implements the algorithm to monitor trends over a period of time in the first electrical signal that comprise at least one of an echo amplitude comprising a diastolic peak of the first signal, a pulse propagation time of the first signal, and a pulse rise time of the first signal that correspond to trends in pressure and trends in interstitial pressure in the region of tissue.

10. The method of claim 9 wherein the processor is further configured to control a pressure in a pneumatic chamber of a cuff used in conjunction with the photoplethysmograph.

11. The method of claim 9 wherein programming the processor to implement the algorithm includes programming to calculate an area under a curve, wherein the curve is determined by a time domain representation of the first signal.

12. A device comprising:
a photoplethysmograph that includes a first sensor configured to be disposed at a surface of a region of tissue, wherein the first sensor has a combination of one or more optical emitters and one or more optical detectors, wherein a spacing of the one or more optical emitters and one or more optical detectors on a surface of the first sensor that interfaces with the surface of the region of tissue is configured to correspond with a selected depth of penetration of light energy into the region of tissue, wherein the first sensor is configured to provide a first electrical signal corresponding to a pressure at the surface of the region of tissue; and
a processor configured to execute instructions to implement an algorithm using the first electrical signal as an input and generate an output corresponding to an internal pressure in the region, wherein the processor implements the algorithm to determine a transmural pressure of the region of tissue from a magnitude of the first electrical signal and wherein the processor implements the algorithm to monitor trends over a period of time in the first electrical signal that comprise at least one of an echo amplitude comprising a diastolic peak of the first signal, a pulse propagation time of the first signal, and a pulse rise time of the first signal that correspond to trends in pressure and trends in interstitial pressure in the region of tissue.

13. The device of claim 12 wherein the photoplethysmograph includes a regional oximeter sensor configured to be disposed at the surface of the region of tissue, wherein the regional oximeter sensor is configured to provide a second electrical signal corresponding to an oxygenation at the surface of the region of tissue, and wherein the processor implements the algorithm using the first electrical signal and the second electrical signal as inputs to generate an output corresponding to the internal pressure in the region.

14. The device of claim 12 wherein the spacing of the one or more optical emitters and one or more optical detectors on the surface of the first sensor is referenced by the processor that implements the algorithm to evaluate the trends over the period of time in the first electrical signal.

15. The device of claim 12 wherein the first signal is referenced to a signal from a control sensor coupled to another region of tissue by the processor that implements the algorithm to evaluate the trends over the period of time in the first electrical signal.

16. The device of claim 12 wherein the pressure is correlated with one or more of a peak value, an average value, a measure of variation, or an area under a curve associated with the first electrical signal that comprise at least one of the echo amplitude of the first signal, the pulse propagation time, and the pulse rise time.

* * * * *

UNITED STATES PATENT AND TRADEMARK OFFICE
CERTIFICATE OF CORRECTION

PATENT NO. : 10,973,417 B2  
APPLICATION NO. : 15/316784  
DATED : April 13, 2021  
INVENTOR(S) : Rausch et al.

Page 1 of 1

It is certified that error appears in the above-identified patent and that said Letters Patent is hereby corrected as shown below:

On the Title Page

On page 2, in Column 2, under "Other Publications", Line 33, delete "Amendmnet" and insert --Amendment-- therefor In the Claims In Column 9, Line 38, in Claim 1, delete "includes," and insert --includes-- therefor Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*